US007149700B1

(12) United States Patent
Munoz et al.

(10) Patent No.: US 7,149,700 B1
(45) Date of Patent: Dec. 12, 2006

(54) METHOD OF DETERMINING TASK COSTS FOR ACTIVITY BASED COSTING MODELS

(75) Inventors: Michael Munoz, Park Ridge, IL (US); Emre Oksan, Mt. Prospect, IL (US)

(73) Assignee: The Whittier Group, Las Vegas, NV (US)

( * ) Notice: Subject to any disclaimer, the term of this patent is extended or adjusted under 35 U.S.C. 154(b) by 0 days.

(21) Appl. No.: 09/316,725

(22) Filed: May 21, 1999

(51) Int. Cl.
*G06F 9/46* (2006.01)
(52) U.S. Cl. ............................... 705/8; 705/2
(58) Field of Classification Search .................. 705/7, 705/8, 9, 10, 400, 2
See application file for complete search history.

(56) References Cited

U.S. PATENT DOCUMENTS

| 5,249,120 | A | * | 9/1993 | Foley .......................... 705/400 |
| 5,732,401 | A | * | 3/1998 | Conway ......................... 705/2 |
| 5,918,219 | A | * | 6/1999 | Isherwood ...................... 705/9 |
| 5,971,585 | A | * | 10/1999 | Dangat et al. .............. 700/102 |
| 6,009,406 | A | * | 12/1999 | Nick ............................ 705/10 |
| 6,073,107 | A | * | 6/2000 | Minkiewicz et al. ........... 705/7 |
| 6,216,108 | B1 | * | 4/2001 | LeVander ....................... 705/7 |

OTHER PUBLICATIONS

Genaidy et al; Computerized predetermined motion-time systems in manufacturing industries; 1990; Computers and Industrial Engineering, vol. 18, No. 4, p571-84; dialog abstract 1 page.*
Dossett, Royal; Work-measured labor standards—The state of the art; Apr. 1995; Engineering v27n4, pp21-25; dialog copy 5 pages.*
Peter F. Drucker, The Information ExecutivesTruly Need, Harvard Business Review, pp. 54-62, Jan.-Feb. 1995.
Kjell B. Zandin, MOST® Work Measurement Systems; 2nd ed., revised and expanded, Chapters 1, 2, 6 and 9 and Appendix A, 1990.
Ralph M. Barnes, Motion and Time Study Design and Measurement of Work; Chapters 1-3, 7-14, 20-23, 27-30 and 36, 1980.

* cited by examiner

*Primary Examiner*—Thomas A Dixon
(74) *Attorney, Agent, or Firm*—Fitch, Even, Tabin & Flannery

(57) ABSTRACT

A method of carrying out activity based costing in a professional practice, such as a healthcare practice or hospital is provided. The costs of activities involving an operator are calculated based on the time the operators should be expected to spend on a task, and the cost overhead, particularly the payment, of the operator. This is achieved using a Pre-Determined Motion Time System such as the MOST® system. This allows the inherent profitability of a business operation to be established independent of the current employees, so that the profitability of the business processes themselves can be ascertained.

18 Claims, 25 Drawing Sheets

| CODE | DESCRIPTION | # OF SLOTS | FEE($) |
|---|---|---|---|
| OFFICE | NEW PATIENT | | |
| 99201 | NEW PT. OFFICE SIMPLE E/M (Lev 1) | 1 | 28.27 |
| 99202 | NEW PT. OFFICE FOCUSED E/M (Lev 2) | 1 | 42.84 |
| 99203 | NEW PT. OFFICE EXPANDED E/M (Lev 3) | 2 | 61.79 |
| 99204 | NEW PT. OFFICE DETAILED E/M (Lev 4) | 2 | 99.61 |
| 99205 | NEW PR. OFFICE COMPLEX E/M (Lev 5) | 4 | 124.89 |
| OFFICE | ESTABLISHED PATIENT | | |
| 99211 | EST. PT. OFFICE SIMPLE (Lev 1) | 1 | 14.01 |
| 99212 | EST. PT. OFFICE FOCUSED (Lev 2) | 1 | 26.8 |
| 99213 | EST. PT. OFFICE EXPANDED (Lev 3) | 1 | 38.26 |
| 99214 | EST. PT. OFFICE DETAILED (Lev 4) | 2 | 57.73 |
| 99205 | EST. PT. OFFICE COMPLEX (Lev 5) | 3 | 84.07 |
| Office | CONSULTS | | |
| 99241 | CONSULT OFFICE SIMPLE E/M (Lev 1) | 1 | 43.99 |
| 99242 | CONSULT OFFICE FOCUSED E/M (Lev 2) | 2 | 67.18 |
| 99243 | CONSULT OFFICE EXPANDED E/M (Lev 3) | 2 | 88.67 |
| 99244 | CONSULT OFFICE DETAILED E/M (Lev 4) | 3 | 123.44 |
| 99245 | CONSULT OFFICE COMPLEX E/M (Lev 5) | 4 | 161.45 |
| 99271 | CONSULT CONF. SIMPLE (Lev 1) | 1 | 40.09 |
| 99272 | CONSULT CONF. FOCUSED (Lev 2) | 1 | 55.84 |
| 99273 | CONSULT CONF. EXPANDED (Lev 3) | 2 | 78.54 |
| 99274 | CONSULT CONF. DETAILED (Lev 4) | 3 | 101.77 |
| 99275 | CONSULT CONF. COMPLEX (Lev 5) | 4 | 141.28 |

| TYPE | EXPLANATION | DR 1 | DR 2 | NP 1 | NP 2 | DR 1 TEAM 1 | DR 1 TEAM 2 | DR 2 TEAM 3 | DR 2 TEAM 4 |
|---|---|---|---|---|---|---|---|---|---|
| OFFICE CODES | | | | | | | | | |
| 1 | NO SHOWS | 37 | 49 | 0 | 0 | 7 | 7 | 42 | 0 |
| 3 | CANCEL APPOINTMENT | 22 | 58 | 0 | 0 | 9 | 15 | 40 | 0 |
| 4 | ADMIT TO HOSPITAL FROM OFFICE | 1 | 6 | 0 | 0 | 0 | 4 | 24 | 0 |
| 5 | NO CHARGE FOR VISIT | 1 | 3 | 0 | 0 | 0 | 1 | 0 | 0 |
| 6 | ALREADY IN HOSPITAL | 6 | 1 | 0 | 0 | 0 | 0 | 2 | 0 |
| 8 | RESCHEDULE | 28 | 45 | 0 | 0 | 12 | 4 | 31 | 0 |
| 9 | IN NURSING HOME | 1 | 1 | 0 | 0 | 0 | 0 | 2 | 0 |
| 10 | END OF FILE | 75 | 49 | 0 | 0 | 1 | 0 | 20 | 0 |
| 12 | WENT TO ER | 0 | 1 | 0 | 0 | 0 | 0 | 3 | 0 |
| 98900 | MED MANAGEMENT | 2 | 4 | 0 | 0 | 0 | 0 | 2 | 0 |
| OFFICE | NEW PATIENT | | | | | | | | |
| 99201 | NEW PT. OFFICE SIMPLE E/M (LEV 1) | 1 | 0 | 1 | 1 | 0 | 0 | 0 | 1 |
| 99202 | NEW PT. OFFICE FOCUSED E/M (LEV 2) | 0 | 0 | 0 | 0 | 0 | 0 | 0 | 0 |
| 99203 | NEW PT. OFFICE EXPANDED E/M (LEV 3) | 0 | 0 | 0 | 0 | 0 | 0 | 0 | 0 |
| 99204 | NEW PT. OFFICE DETAILED E/M (LEV 4) | 0 | 0 | 0 | 0 | 0 | 0 | 0 | 0 |
| 99205 | NEW PT. OFFICE COMPLEX E/M (LEV 5) | 1 | 0 | 1 | 1 | 0 | 0 | 0 | 1 |
| | TOTAL NEW PATIENT | | | | | | | | |
| OFFICE | ESTABLISHED PATIENT | | | | | | | | |
| 99211 | EST. PT. OFFICE SIMPLE (LEV 1) | 5 | 4 | 1 | 1 | 2 | 0 | 5 | 0 |
| 99212 | EST. PT. OFFICE FOCUSED (LEV 2) | 56 | 58 | 0 | 0 | 52 | 72 | 95 | 0 |
| 99213 | EST. PT. OFFICE EXPANDED (LEV 3) | 641 | 841 | 0 | 0 | 146 | 153 | 659 | 0 |
| 99214 | EST. PT. OFFICE DETAILED (LEV 4) | 346 | 325 | 0 | 0 | 28 | 30 | 25 | 0 |
| 99215 | EST. PT. OFFICE COMPLEX (LEV 5) | 1 | 0 | 0 | 1 | 0 | 0 | 0 | 0 |
| | TOTAL ESTABLISHED PATIENT | 1049 | 1228 | 1 | 1 | 228 | 255 | 784 | 0 |

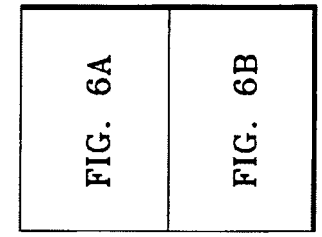

| | | | | | | | | | | | | |
|---|---|---|---|---|---|---|---|---|---|---|---|---|
| OFFICE | CONSULTS | | | | | | | | | | | |
| 99241 | CONSULT OFFICE SIMPLE E/M (LEV 1) | 1 | 1 | 0 | 0 | 0 | 0 | 0 | 0 | 0 | 0 | 0 |
| 99242 | CONSULT OFFICE FOCUSED E/M (LEV 2) | 0 | 0 | 0 | 0 | 0 | 0 | 0 | 0 | 0 | 0 | 0 |
| 99243 | CONSULT OFFICE EXPANDED E/M (LEV 3) | 0 | 0 | 0 | 0 | 0 | 0 | 0 | 0 | 0 | 0 | 0 |
| 99244 | CONSULT OFFICE DETAILED E/M (LEV 4) | 0 | 0 | 0 | 0 | 0 | 0 | 0 | 0 | 0 | 0 | 0 |
| 99245 | CONSULT OFFICE COMPLEX E/M (LEV 5) | 0 | 0 | 0 | 0 | 0 | 0 | 0 | 0 | 0 | 0 | 0 |
| 99271 | CONSULT CONF. SIMPLE (LEV 1) | 0 | 0 | 0 | 0 | 0 | 0 | 0 | 0 | 0 | 0 | 0 |
| 99272 | CONSULT CONF. FOCUSED (LEV 2) | 0 | 0 | 0 | 0 | 0 | 0 | 0 | 0 | 0 | 0 | 0 |
| 99273 | CONSULT CONF. EXPANDED (LEV 3) | 0 | 0 | 0 | 0 | 0 | 0 | 0 | 0 | 0 | 0 | 0 |
| 99274 | CONSULT CONF. DETAILED (LEV 4) | 0 | 0 | 0 | 0 | 0 | 0 | 0 | 0 | 0 | 0 | 0 |
| 99275 | CONSULT CONF. COMPLEX (LEV 5) | 1 | 1 | 0 | 0 | 0 | 0 | 0 | 0 | 0 | 0 | 0 |
| | TOTAL OFFICE CONSULTS | | | | | | | | | | | |
| HOSPITAL | | | | | | | | | | | | |
| 99217 | OBSERVATION CARE/DISCHARGE DAY MANG | 0 | 0 | 0 | 0 | 0 | 0 | 0 | 0 | 0 | 0 | 0 |
| 99218 | INITIAL OBSERVATION/BASIC | 0 | 0 | 0 | 0 | 0 | 0 | 0 | 0 | 0 | 0 | 0 |
| 99219 | INITIAL OBSERVATION/MODERATE | 0 | 0 | 0 | 0 | 0 | 0 | 0 | 0 | 0 | 0 | 0 |

| TYPE | EXPLANATION | FEE($) PER OOS | DR 1 | DR 2 |
|---|---|---|---|---|
| OFFICE CODES | | | | |
| 1 | NO SHOWS | | | |
| 3 | CANCEL APPOINTMENT | | | |
| 4 | ADMIT TO HOSPITAL FROM OFFICE | | | |
| 5 | NO CHARGE FOR VISIT | | | |
| 6 | ALREADY IN HOSPITAL | | | |
| 8 | RESCHEDULE | | | |
| 9 | IN NURSING HOME | | | |
| 10 | END OF FILE | | | |
| 12 | WENT TO ER | | | |
| 98900 | MED MANAGEMENT | 28.27 | 28.27 | 0 |
| OFFICE | NEW PATIENT | | | |
| 99201 | NEW PT. OFFICE SIMPLE E/M (LEV 1) | 42.84 | 0 | 0 |
| 99202 | NEW PT. OFFICE FOCUSED E/M (LEV 2) | 61.79 | 0 | 0.006179 |
| 99203 | NEW PT. OFFICE EXPANDED E/M (LEV 3) | 99.61 | 0 | 0.009961 |
| 99204 | NEW PT. OFFICE DETAILED E/M (LEV 4) | 124.89 | 0 | 0.012489 |
| 99205 | NEW PT. OFFICE COMPLEX E/M (LEV 5) | | 28 | 0 |
| | TOTAL NEW PATIENT | | | |
| OFFICE | ESTABLISHED PATIENT | | | |
| 99211 | EST. PT. OFFICE SIMPLE (LEV 1) | 14.01 | 70.05 | 56.04 |
| 99212 | EST. PT. OFFICE FOCUSED (LEV 2) | 26.8 | 1500.8 | 58 |
| 99213 | EST. PT. OFFICE EXPANDED (LEV 3) | 38.26 | 24524.66 | 841 |
| 99214 | EST. PT. OFFICE DETAILED (LEV 4) | 57.73 | 19974.58 | 325 |
| 99215 | EST. PT. OFFICE COMPLEX (LEV 5) | 84.07 | 84.07 | 0 |
| | TOTAL ESTABLISHED PATIENT | | 46154 | 1228 |

Fig. 7B

| NP 1 | NP 2 | DR 1 TEAM 1 | DR 1 TEAM 2 | DR 2 TEAM 3 | DR 2 TEAM 4 |
|---|---|---|---|---|---|
| 28.27 | 28.27 | 0 | 0 | 0 | 28.27 |
| 0 | 0 | 0 | 0 | 0 | 0 |
| 0 | 0 | 0 | 0 | 0.006179 | 0 |
| 0 | 0 | 0.012489 | 0 | 0.009961 | 0 |
| 0 | 28 | 0 | 0 | 0.012489 | 28 |
| 14.01 | 14.01 | 28.02 | 0 | 0 | 0 |
| 1554.4 | 0 | 1393.6 | 1929.6 | 70.05 | 0 |
| 32176.66 | 0 | 5585.96 | 5853.78 | 2546 | 0 |
| 18762.25 | 0 | 616.44 | 1731.9 | 25213.34 | 0 |
| 0 | 0 | 0 | 0 | 1443.25 | 0 |
| 52549 | 14 | 8624 | 9515 | 29273 | 0 |

| | | | |
|---|---|---|---|
| OFFICE | CONSULTS | | |
| 99241 | CONSULT OFFICE SIMPLE E/M (LEV 1) | 43.99 | 43.99 43.99 |
| 99242 | CONSULT OFFICE FOCUSED E/M (LEV 2) | 67.18 | 0 0 |
| 99243 | CONSULT OFFICE EXPANDED E/M (LEV 3) | 86.67 | 0 0 |
| 99244 | CONSULT OFFICE DETAILED E/M (LEV 4) | 123.44 | 0 0 |
| 99245 | CONSULT OFFICE COMPLEX E/M (LEV 5) | 161.45 | 0 0 |
| 99271 | CONSULT CONF. SIMPLE (LEV 1) | 40.09 | 0 0 |
| 99272 | CONSULT CONF. FOCUSED (LEV 2) | 55.84 | 0 0 |
| 99273 | CONSULT CONF. EXPANDED (LEV 3) | 78.54 | 0 0 |
| 99274 | CONSULT CONF. DETAILED (LEV 4) | 101.77 | 0 0 |
| 99275 | CONSULT CONF. COMPLEX (LEV 5) | 141.28 | 0.014128 0.001413 |
| | TOTAL OFFICE CONSULTS | | 44 44 |
| HOSPITAL | | | |
| 99217 | OBSERVATION CARE/DISCHARGE DAY MANG | 61.91 | 0 0 |
| 99218 | INITIAL OBSERVATION/BASIC | 62.15 | 0 0 |
| 99219 | INITIAL OBSERVATION/MODERATE | 93.72 | 0 0 |

Fig. 7C

| FIG. 7A | FIG. 7B |
|---|---|
| FIG. 7C | FIG. 7D |

PROVIDER BUSINESS LINE OOS TOTALS

|          | DR 1 | DR 2 | NP 1 | NP 2 | DR 1 TEAM 1 | DR 1 TEAM 2 | DR 2 TEAM 3 | DR 2 TEAM 4 | PRACTICE |
|----------|------|------|------|------|-------------|-------------|-------------|-------------|----------|
| OFFICE   | 1051 | 1229 | 2    | 2    | 228         | 255         | 784         | 1           | 3552     |
| HOSPITAL | 27   | 42   | 0    | 0    | 0           | 0           | 0           | 0           | 69       |
| SNF      | 4    | 4    | 1164 | 1170 | 4           | 4           | 4           | 4           | 2358     |
| CPO      | 1    | 1    | 1    | 1    | 1           | 1           | 1           | 1           | 8        |
| DRG      | 1    | 1    | 0    | 0    | 0           | 0           | 0           | 0           | 2        |
|          | 1084 | 1277 | 1167 | 1173 | 233         | 260         | 789         | 6           | 5989     |

PROVIDER DISTRIBUTION

|          | DR 1   | DR 2  | NP 1  | NP 2  | DR 1 TEAM 1 | DR 1 TEAM 2 | DR 2 TEAM 3 | DR 2 TEAM 4 |      |
|----------|--------|-------|-------|-------|-------------|-------------|-------------|-------------|------|
| OFFICE   | 29.59% | 34.6% | 0.1%  | 0.1%  | 6.4%        | 7.2%        | 22.1%       | 0.0%        | 100% |
| HOSPITAL | 39.1%  | 60.9% | 0.0%  | 0.0%  | 0.0%        | 0.0%        | 0.0%        | 0.0%        | 100% |
| SNF      | 0.2%   | 0.2%  | 49.4% | 49.4% | 0.2%        | 0.2%        | 0.2%        | 0.2%        | 100% |
| CPO      | 12.5%  | 12.5% | 12.5% | 12.5% | 12.5%       | 12.5%       | 12.5%       | 12.5%       | 100% |
| DRG      | 50.0%  | 50.0% | 0.0%  | 0.0%  | 0.0%        | 0.0%        | 0.0%        | 0.0%        | 100% |

PRODUCT LINE DISTRIBUTION FOR PRACTICE

|          | PRACTICE |
|----------|----------|
| OFFICE   | 59.3%    |
| HOSPITAL | 1.2%     |
| SNF      | 39.4%    |
| CPO      | 0.1%     |
| DRG      | 0.0%     |
|          | 100%     |

| | | OFFICE | HOSPITAL | NURSING HOME | CPO | DRUG | |
|---|---|---|---|---|---|---|---|
| | | 90% | 2% | 2% | 0% | 6% | 100% |
| RENT | 5000 | 90% | 2% | 2% | 0% | 6% | 100% |
| UTILITIES | | | | | | | 0% |
| ELECTRICITY | 500 | 90% | 2% | 2% | 0% | 6% | 100% |
| WATER | 200 | 90% | 2% | 2% | 0% | 6% | 100% |
| GAS | 100 | 90% | 2% | 2% | 0% | 6% | 100% |
| TELEPHONE | 800 | 59% | 1% | 39% | 0% | 0% | 100% |
| PRACTICE SUPPLIES | | | | | | | 0% |
| MEDICAL PRACTICE | 200 | 99% | 0% | 0% | 0% | 1% | 100% |
| OFFICE SUPPLIES | 200 | 90% | 4% | 4% | 1% | 1% | 100% |
| ADMINISTRATIVE SALARIES | 3500 | 59% | 1% | 39% | 0% | 0% | 100% |
| MEDICAL EQUIPMENT | 500 | 99% | 0% | 0% | 0% | 1% | 100% |
| INTEREST ON BORROWING | 500 | 59% | 1% | 39% | 0% | 0% | 100% |
| COMPUTER EXPENSES | 600 | 59% | 1% | 39% | 0% | 0% | 100% |
| | 12100 | | | | | | |

FIG. 10

| | OFFICE | HOSPITAL | NURSING HOME | CPO | DRUG | |
|---|---|---|---|---|---|---|
| RENT | 4,500.00 | 100.00 | 100.00 | — | — | |
| UTILITIES | | | | | | |
| ELECTRICITY | 450.00 | 10.00 | 10.00 | — | 30.00 | |
| WATER | 180.00 | 4.00 | 4.00 | — | 12.00 | |
| GAS | 90.00 | 2.00 | 2.00 | — | 6.00 | |
| TELEPHONE | 474.47 | 9.22 | 9.22 | 1.07 | 0.27 | |
| PRACTICE SUPPLIES | | | | | | |
| MEDICAL PRACTICE | 198.00 | — | — | — | 2.00 | |
| OFFICE SUPPLIES | 180.00 | 8.00 | 8.00 | 2.00 | 2.00 | |
| ADMINISTRATIVE SALARIES | 2,075.81 | 40.32 | 1,378.03 | 4.68 | 1.17 | |
| MEDICAL EQUIPMENT | 495.00 | — | — | — | 5.00 | |
| INTEREST ON BORROWING | 296.54 | 5.76 | 196.86 | 0.67 | 0.17 | |
| COMPUTER EXPENSES | 355.85 | 6.91 | 236.23 | 0.80 | 0.20 | |
| | 9,295.67 | 186.21 | 2,250.10 | 9.21 | 358.80 | 12,100.00 |

Fig. 11A

| | FIG. 11A |
|---|---|
| | FIG. 11B |

FREQUENCIES USED IN CALCULATIONS

| DESCRIPTION | UNIT OF MEASURE | FREQUENCY | DEPARTMENT |
|---|---|---|---|
| RECEPTIONIST WEEKLY FIXED ACTIVITIES | MINUTES | 543.37 | RECEPTION |
| NUMBER OF PT IN RECALL LIST | MONTH | 20.00 | RECEPTION |
| NUMBER OF WALK-IN PT | MONTH | 25.00 | RECEPTION |
| NUMBER OF CO-PAYMENTS | MONTH | 60.00 | RECEPTION |
| NUMBER OF PH. CALLS TRANSFERED | MONTH | 6888.00 | RECEPTION |
| MEDICAL ASSISTANT WEEKLY FIXED ACTIVITIES | MINUTES | 1188.81 | MED ASST. |
| % OF PT PREEXAM TESTS PERFORMED | PATIENTS | 17.500% | MED ASST. |
| NUMBER OF BLOOD DRAWS DONE BY MA | MONTH | 40.00 | MED ASST. |
| % OF PT PRESCRIPTION INSTR. ARE WRITTEN | PATIENTS | 33.00% | MED ASST. |
| % OF REFERRALS MA MAKES THE APPOINTMENT | REFERRALS | 16.50% | MED ASST. |
| % OF DIAGNOSTIC TEST MA MAKES THE APPT. | DIAGNOSTIC | 16.50% | MED ASST. |
| NUMBER OF PRESCRIPTION REFILLS PROCESSED | MONTH | 400.00 | MED ASST. |
| TRANSCRIPTION WEEKLY FIXED ACTIVITIES | MINUTES | 127.65 | TRANSCRIPTION |
| # OF OFFICE PT DICTATION PER TAPE | TAPE | 15.00 | TRANSCRIPTION |
| # OF HOSPITAL PT DICTATION PER TAPE | TAPE | 6.00 | TRANSCRIPTION |
| # OF CPO PT DICTATION PER TAPE | TAPE | 30.00 | TRANSCRIPTION |
| # OF TIMES OFFICE PT DOCUMENTS FAXED BY PHYSICIAN ORDER | MONTH | 5.00 | TRANSCRIPTION |
| # OF H&P FAXED TO HOSPITAL | MONTH | 40.00 | TRANSCRIPTION |
| TRIAGE WEEKLY FIXED ACTIVITIES | MINUTES | 396.75 | TRIAGE |
| # OF FAXES PROCESSED BY TRIAGE FOR OFFICE PT | MONTH | 500.00 | TRIAGE |

Fig. 11B

| DESCRIPTION | UNIT OF MEASURE | FREQUENCY | DEPARTMENT |
|---|---|---|---|
| # OF FAXES PROCESSED BY TRIAGE FOR HOSP. PT | MONTH | 350.00 | TRIAGE |
| # OF FAXES PROCESSED BY TRIAGE FOR SNF PT | MONTH | 1150.00 | TRIAGE |
| # OF TIMES DOCUMENTS FAXED BY PHYS. ORDER | MONTH | 70.00 | TRIAGE |
| # OF NARCOTIC PRESCRIPTIONS REFILLS PROCESSED | MONTH | 40.00 | TRIAGE |
| # OF PH. CONVERSATIONS WITH PT OR FAMILIES | MONTH | 810.00 | TRIAGE |
| # OF PH. CALLS FOR REFERRALS & OTHER CALLS | MONTH | 558.25 | TRIAGE |
| # OF PH. CALLS TO PHARMACY FOR PRESCRIPTION REFILLS | MONTH | 230.00 | TRIAGE |
| # OF PHONE CALLS FROM SNF | MONTH | 322.35 | TRIAGE |
| # OF H&P FAXED TO HOSPITAL | MONTH | 33.00 | TRIAGE |
| # OF HOSP. REFERRALS MANAGED (ORGANIZED) | MONTH | 33.00 | TRIAGE |
| # OF LAB REPORTS RECEIVED THROUGH PRINTER (SNF) | MONTH | 200.00 | TRIAGE |
| % OF CPO CALLS HANDLED BY TRIAGE | MONTH | 20% | TRIAGE |
| BILLING WEEKLY FIXED ACTIVITIES | MINUTES | 2703.65 | BILLING |
| # OF REBILLINGS PERFORMED | MONTH | 400.00 | BILLING |
| # OF PRIVATE BILLS | MONTH | 300.00 | BILLING |
| # OF ACCOUNTS IN COLLECTION PROCEDURE | MONTH | 75.00 | BILLING |
| # OF PHONE CALLS | MONTH | 800.00 | BILLING |
| MEDICAL RECORDS WEEKLY FIXED ACTIVITIES | MINUTES | 155.25 | MED. REC. |
| AVERAGE # OF HANDLING DOCUMENTS PER OFFICE PT CHART | PER VISIT | 3.00 | MED. REC. |
| AVERAGE # OF HANDLING DOCUMENTS PER HOSPITAL PT CHART | PER VISIT | 5.00 | MED. REC. |
| AVERAGE # OF HANDLING DOCUMENTS PER SNF PT CHART | PER VISIT | 1.00 | MED. REC. |
| AVERAGE # OF HANDLING DOCUMENTS PER CPO PT CHART | PER CALL | 1.00 | MED. REC. |
| # OF FAXED DOCUMENTS BY PHYSICIAN REQUEST | MONTH | 80.00 | MED. REC. |

| OFFICE | MON | TUE | WED | THUR | FRI | |
|---|---|---|---|---|---|---|
| DOCTOR 1 | 13 | 18 | 10 | 10 | 10 | 61 |
| DOCTOR 2 | 24 | 0 | 0 | 20 | 20 | 64 |
| NP 1 | 24 | 14 | 14 | 0 | 0 | 52 |
| NP 2 | 10 | 10 | 12 | 0 | 24 | 56 |
| | | | | | | 233 |

| HOSPITAL | MON | TUE | WED | THUR | FRI | |
|---|---|---|---|---|---|---|
| DOCTOR 1 | 20 | 0 | 0 | 20 | 23.33 | 63.33 |
| DOCTOR 2 | 0 | 20 | 25 | 10 | 13.33 | 68.33 |
| | | | | | | 131.66 |

| SNF | MON | TUE | WED | THUR | FRI | |
|---|---|---|---|---|---|---|
| DOCTOR 1 | 1 | 0 | 0 | 0 | 0 | 1 |
| DOCTOR 2 | 1 | 0 | 0 | 0 | 0 | 1 |
| NP 1 | 0 | 14 | 14 | 26 | 26 | 80 |
| NP 2 | 18 | 16 | 14 | 26 | 0 | 74 |
| | | | | | | 156 |

| DRG | MON | TUE | WED | THUR | FRI | |
|---|---|---|---|---|---|---|
| DOCTOR 1 | 0 | 0 | 0 | 0 | 0 | 8 |
| DOCTOR 2 | 0 | 0 | 5 | 0 | 0 | 2 |
| | | | | | | 10 |

| CPO | MON | TUE | WED | THUR | FRI | |
|---|---|---|---|---|---|---|
| DOCTOR 1 | 0 | 0 | 0 | 5 | 0 | 5 |
| DOCTOR 2 | 0 | 0 | 5 | 0 | 0 | 5 |
| | | | | | | 10 |

| PROVIDER SCHEDULE | MON | TUE | WED | THUR | FRI | TOTAL |
|---|---|---|---|---|---|---|
| DOCTOR 1 | 8.50 | 4.50 | 4.50 | 8.75 | 8.33 | 34.6 |
| DOCTOR 2 | 6.25 | 5.00 | 8.00 | 7.50 | 8.33 | 35.1 |
| NP 1 | 6.00 | 7.00 | 7.00 | 6.50 | 6.50 | 33.0 |
| NP 2 | 7.00 | 6.50 | 6.50 | 6.50 | 6.00 | 32.5 |
| | | | | | | 135.17 |

TEAM BUSINESS LINE DISTRIBUTION

| | OFFICE | HOSPITAL | SNF | CPO |
|---|---|---|---|---|
| PHYSICIAN % | 10% | 100% | 40% | 100% |
| NP% | 90% | 0% | 60% | 0% |

| BUSINESS LINE PT OPERATING HOURS | |
|---|---|
| OFFICE | 7.25 |
| HOSPITAL | 5 |
| SNF | 7.8 |
| CPO | 7.8 |

| PROVIDER SALARY INFORMATION | |
|---|---|
| DOCTOR 1 | $10,000 |
| DOCTOR 2 | $10,000 |
| NP1 | $ 4,767 |
| NP2 | $4,050 |
| BENEFITS | 30% |

PROVIDER WEEKLY HOURS
(EXCLUDING SPECIAL PROJECTS)
(WOUND CARE)

| DOCTOR 1 | 40 |
|---|---|
| DOCTOR 2 | 30 |
| NP1 | 40 |
| NP2 | 40 |
| | 150 |

Fig. 12

| BUSINESS LINE | BUSINESS LINE HOURS | PERCENTAGE | ALLOCATION UNUSED PROVIDER HOURS |
|---|---|---|---|
|  |  |  | 61.34 |
| OFFICE | 233 | 43.26% | 26.53291501 |
| HOSPITAL | 132 | 24.44% | 14.99280511 |
| SNF | 156 | 28.96% | 17.776452679 |
| CPO | 10 | 1.86% | 1.138751717 |
| DRG | 8 | 1.49% | 0.911001374 |
|  | 538.66 | 100.00% |  |

PER MINUTE COST OF PROVIDERS

| | NP TEAM% | MONTHLY | BENEFITS | TOTAL | PER MINUTE |
|---|---|---|---|---|---|
| DOCTOR 1 |  | $10,000 | $3,000 | $13,000 | $1.42 |
| DOCTOR 2 |  | $10,000 | $3,000 | $13,000 | $1.89 |
| NP1 |  | $ 4,767 | $1,430 | $ 6,197 | $0.68 |
| NP2 |  | $ 4,050 | $1,215 | $ 5,265 | $0.57 |
| TEAM 1-OFFICE | 90% |  |  | $ 6,877 | $0.75 |
| TEAM 1-SNF | 60% |  |  | $ 8,918 | $0.97 |
| TEAM 2-OFFICE | 90% |  |  | $ 6,039 | $0.66 |
| TEAM 2-SNF | 60% |  |  | $ 8,359 | $0.91 |
| TEAM 3-OFFICE | 90% |  |  | $ 6,877 | $0.80 |
| TEAM 3-SNF | 60% |  |  | $ 8,918 | $1.16 |
| TEAM 4-OFFICE | 90% |  |  | $ 6,039 | $0.71 |
| TEAM 4-SNF | 60% |  |  | $ 8,359 | $1.10 |

SUPPORT STAFF AVERAGE HOURS WORKED PER DAY

| DEPARTMENT | |
|---|---|
| RECEPTION | 16 |
| MEDICAL ASSISTANTS | 16 |
| TRANSCRIPTION | 8 |
| TRIAGE | 10 |
| BILLING | 16 |
| MEDICAL RECORDS | 6.4 |

SUPPORT STAFF SALARY TABLES

| RECEPTION | $3,467 |
|---|---|
| MEDICAL ASSISTANTS | $3,983 |
| TRANSCRIPTION | $2,202 |
| TRIAGE | $4,167 |
| BILLING | $3,886 |
| MEDICAL RECORDS | $1,241 |
| BENEFIT % | 30% |

BUSINESS LINE PT OPERATING HOURS

| OFFICE | 7.25 |
|---|---|
| HOSPITAL | 5 |
| SNF | 7.8 |
| CPO | 7.8 |

PER MINUTE COST SUPPORT STAFF

| DEPARTMENT SALARY TABLE | MONTHLY | BENEFITS | TOTAL | PER MINUTE |
|---|---|---|---|---|
| RECEPTION | $3,467 | $1,040 | $4,507 | $0.25 |
| MEDICAL ASSISTANTS | $3,983 | $1,195 | $5,178 | $0.28 |
| TRANSCRIPTION | $2,202 | $ 661 | $2,863 | $0.31 |
| TRIAGE | $4,167 | $1,253 | $5,428 | $0.47 |
| BILLING | $3,886 | $1,166 | $5,052 | $0.28 |
| MEDICAL RECORDS | $1,241 | $ 372 | $1,163 | $0.22 |

| | RECEPTIONIST | | | | |
|---|---|---|---|---|---|
| | MONTHLY FIXED ACTIVITIES | RECALL PROGRAMS | SCHEDULE APPOINTMENT | CANCEL APPT. AND RESCHEDULE | SCHEDULE NEW PATIENT APPOINTMENT |
| PRACTICE FREQUENCY | 2173.50 | 20.00 | 502.20 | 263.71 | 4.00 |
| TASK TIME | N/A | N/A | N/A | N/A | N/A |
| (%) OF OOS | N/A | N/A | N/A | N/A | N/A |
| CUM. DEPT. ACTIVITY (Min.) | 0.61 | 0.62 | 0.86 | 0.99 | 3.53 |
| CUM. PRACTICE ACTIVITY (Min.) | 0.61 | 0.62 | 0.86 | 0.99 | 3.53 |
| ACTIVITY COST / OOS ($) | 0.15 | 0.00 | 0.06 | 0.03 | 0.62 |
| CUM. DEPT. ACTIVITY COST | 0.15 | 0.15 | 0.21 | 0.24 | 0.87 |
| CUM. PRACTICE ACTIVITY COST | 0.15 | 0.15 | 0.21 | 0.24 | 0.87 |
| MONTHLY MONTHLY ACTIVITY COST ($) | — | — | — | — | — |
| CUM. MON. DEPT. COST ($) | 534.73 | 8.70 | 241.67 | 173.39 | 9.98 |
| CUM. MON. PRACTICE COST ($) | 534.73 | 543.43 | 785.09 | 958.48 | 968.47 |
| | 534.73 | 543.43 | 785.09 | 958.48 | 968.47 |

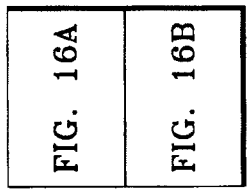

FIG. 16

| FIG. 16A |
|---|
| FIG. 16B |

| PHYSICIAN 1 | | | | | |
|---|---|---|---|---|---|
| FREQUENCY | 643.12 | 5.92 | 143.10 | 50 | 1 |
| TASK TIME | 0.61 | 1.7682 | 1.958 | N/A | N/A |
| (%) OF OOS | 100% | 0.56% | 13.62% | 4.76% | 0.10% |
| CUM. DEPT. ACTIVITY (Min.) | 0.61 | 0.62 | 0.89 | 0.99 | 3.53 |
| CUM. PRACTICE ACTIVITY (Min.) | 0.61 | 0.62 | 0.89 | 0.99 | 3.53 |
| ACTIVITY COST / OOS ($) | 0.15 | 0.00 | 0.07 | 0.03 | 0.00 |
| CUM. DEPT. ACTIVITY COST | 0.15 | 0.15 | 0.22 | 0.25 | 0.25 |
| CUM. PRACTICE ACTIVITY COST | 0.15 | 0.15 | 0.22 | 0.25 | 0.25 |
| MONTHLY | | | | | |
| MONTHLY ACTIVITY COST ($) | 158.22 | 8.70 | 68.86 | 32.87 | 2.50 |
| CUM. MON. DEPT. COST ($) | 158.22 | 543.43 | 229.66 | 262.53 | 265.03 |
| CUM. MON. PRACTICE COST ($) | 534.73 | 158.22 | 229.66 | 262.53 | 265.03 |

FIG. 16B

| | OFFICE | HOSPITAL | SNF | CPO | DRG |
|---|---|---|---|---|---|
| RECEPTIONIST | 10.94 | 2.06 | — | — | — |
| MEDICAL ASSISTANT | 15.97 | 0.92 | — | — | — |
| TRANSCRIPTION | 12.68 | 31.11 | 10.6 | 5.34 | — |
| TRIAGE | 1.90 | 36.90 | 1.62 | 10.26 | — |
| BILLING | 10.37 | 15.17 | 7.81 | 10.63 | — |
| MEDICAL RECORDS | 4.69 | 7.73 | 1.63 | 3.49 | — |
| PROVIDER | 20.39 | 38.96 | 25.52 | 53.00 | — |

FIG. 17

| PROVIDER CAPACITY | SLOTS PER OOS | SLOTS DEDICATED | MAX. PATIENT/DAY | MAX. PT PER HOUR | CURRENT PT PER HOUR |
|---|---|---|---|---|---|
| OFFICE | 1.21 | 233 | 38.42 | 5.3 | 23.61 |
| HOSPITAL | 1.71 | 131.66 | 15.40 | 3.08 | 0.67 |
| SNF | 1.67 | 156 | 18.73 | 2.40 | 14.57 |
| CPO | 2.88 | 10 | 0.70 | 0.09 | 0.05 |
| DRG | 1.00 | 10 | 2.00 | 0.28 | 0.01 |

| | RESTRICTIVE Min/OOS | NONRESTRICTIVE Min/OOS | MINIMUM COVERAGE/HR. | UNUTILIZED PORTION | U.P. COVERAGE |
|---|---|---|---|---|---|
| RECEPTIONIST | 4.71 | 8.29 | 0.42 | 0.58 | 80.77 |
| MEDICAL ASSISTANT | 7.95 | 8.93 | 0.70 | 0.30 | 41.16 |
| TRANSCRIPTION | 0 | 12.06 | 0.00 | 2.00 | 276.71 |
| TRIAGE | 0 | 12.2 | 0.00 | 2.00 | 276.71 |
| BILLING | 0 | 9.41 | 0.00 | 2.00 | 276.71 |
| MEDICAL RECORDS | 0 | 3.52 | 0.00 | 2.00 | 276.71 |
| PROVIDER | 25.90 | 2.07 | 5.32 | 0.68 | 87.20 |
| PROVIDER (OFFICE) | 19.62 | 3.00 | 7.72 | 0.28 | 38.60 |
| PROVIDER (HOSPITAL) | 32.35 | 6.00 | 1.66 | 0.34 | 47.01 |
| PROVIDER (SNF) | 24.99 | 5.00 | 6.07 | 0.93 | 129.04 |
| PROVIDER (CPO) | 0 | 43.13 | 0.00 | 0.00 | 0.00 |
| PROVIDER (DRG) | 0 | 15.00 | 1.00 | 0.00 | 0.00 |

| | REQUIRED NON-RESTRICTIVE (HSR) | REQ. U.P. DIFFERENCE | MINIMUM STAFF HOURS | TOTAL HRS. | UTILIZATION RATIO |
|---|---|---|---|---|---|
| RECEPTIONIST | 490.66 | 409.89 | 138.35 | 548.25 | 180% |
| MEDICAL ASSISTANT | 528.67 | 487.51 | 138.35 | 625.86 | 205% |
| TRANSCRIPTION | 1199.36 | 922.65 | 276.71 | 1199.36 | 786% |
| TRIAGE | 204.16 | −72.55 | 276.71 | 204.16 | 107% |
| BILLING | 919.23 | 642.52 | 276.71 | 919.23 | 301% |
| MEDICAL RECORDS | 350.31 | 73.60 | 276.71 | 350.31 | 287% |
| PROVIDER | 53.74 | −33.46 | 764.86 | 731.40 | 100% |
| PROVIDER (OFFICE) | 177.60 | 193.00 | 1106.83 | 1245.84 | 503% |
| PROVIDER (HOSPITAL) | 6.90 | −40.11 | 276.71 | 236.60 | 169% |
| PROVIDER (SNF) | 196.50 | 67.46 | 968.48 | 1035.94 | 625% |
| PROVIDER (CPO) | 1.77 | 1.77 | 0.00 | 1.77 | 17% |
| PROVIDER (DRG) | 0.11 | 0.11 | 0.00 | 0.0011 | 17% |

FIG. 20

CUMULATIVE DEPARTMENT HOURS BASED ON HISTORICAL MONTHLY WORKLOAD

| SBU | OFFICE | HOSPITAL | SNF | CPO | DRG | TOTAL | UTILIZATION ACTUAL | RATIOS %(1) | %(2) |
|---|---|---|---|---|---|---|---|---|---|
| DEPARTMENT | | | | | | | | | |
| RECEPTION | 498.0 | 2.4 | — | — | — | 500 | 305 | 164% | 180% |
| MEDICAL ASSISTANTS | 727.0 | 1.2 | — | — | — | 728 | 305 | 239% | 205% |
| TRANSCRIPTION | 746.9 | 35.5 | 416.7 | 0.2 | — | 1199 | 153 | 786% | 786% |
| TRIAGE | 102.2 | 42.4 | 59.2 | 0.3 | — | 204 | 191 | 107% | 107% |
| BILLING | 602.3 | 12.5 | 304.1 | 0.4 | — | 919 | 305 | 301% | 301% |
| MEDICAL RECORDS | 277.1 | 8.9 | 64.2 | 0.1 | — | 350 | 122 | 287% | 287% |
| | | | | | | | | | |
| PROVIDER (OFFICE) | 1318 | | | | | 1318 | 248 | 532% | 503% |
| PROVIDER (HOSP.) | | 39 | | | | 39 | 140 | 28% | 169% |
| PROVIDER (SNF) | | | 1218 | | | 1218 | 166 | 734% | 625% |
| PROVIDER (CPO) | | | | 2 | | 2 | 11 | 17% | 17% |
| PROVIDER (DRG) | | | | | 0.11 | 0 | 9 | 1% | 1% |
| | | | | | | | | | |
| PROVIDER | 1318 | 39 | 1218 | 2 | 0 | | | | |
| | | | | | | | | | |
| PROVIDER (DR1) | 418.4 | 13.3 | 1.4 | 0.7 | 0.0 | 434 | 116 | 375% | |
| PROVIDER (DR2) | 476.1 | 25.4 | 1.4 | 1.1 | 0.1 | 504 | 108 | 4675 | |
| PROVIDER (NP1) | 0.6 | — | 602.9 | — | — | 604 | −165 | −365% | |
| PROVIDER (NP2) | 0.6 | — | 606.5 | — | — | 607 | 49 | 1235% | |
| | | | | | | | | | |
| TEAM 1 | 76.0 | — | 1.4 | — | — | 77 | 77 | 100% | |
| TEAM 2 | 85.0 | — | 1.4 | — | — | 86 | 86 | 100% | |
| TEAM 3 | 261.3 | — | 1.4 | — | — | 263 | 263 | 100% | |
| TEAM 4 | 0.3 | — | 1.4 | — | — | 2 | 2 | 100% | |
| | | | | | | | | | |
| TOTAL DR1 | | | | | | 451 | 133 | 339.7% | |
| TOTAL DR2 | | | | | | 531 | 135 | 393.1% | |
| TOTAL NP1 | | | | | | 909 | 140 | 649.4% | |
| TOTAL NP2 | | | | | | 686 | 128 | 537.1% | |
| | | | | | | 2577 | 536 | 481.1% | |

|  | OFFICE | HOSPITAL | SNF |
|---|---|---|---|
| PROVIDER (DR1) | 6.18 | 0.18 | 2.10 |
| PROVIDER (DR2) | 6.81 | 0.31 | 2.10 |
| PROVIDER (NP1) | 5.07 | – | 6.30 |
| PROVIDER (NP2) | 1.2 | – | 6.85 |

| ADJUSTMENT | 0.87 | 0.84 | 0.83 |
|---|---|---|---|

| DEPARTMENT SALARY TABLE | UNUTILZED LABOR |
|---|---|
| RECEPTION | 0 |
| MEDICAL ASSISTANTS | 0 |
| TRANSCRIPTION | 0 |
| TRIAGE | 0 |
| BILLING | 0 |
| MEDICAL RECORDS | 0 |

| PROVIDER SALARY TABLE | UNUTILZED LABOR |
|---|---|
| PROVIDER (DR1) | 0 |
| PROVIDER (DR2) | 0 |
| PROVIDER (NP1) | 0 |
| PROVIDER (NP2) | 0 |
| TEAM 1 | 0 |
| TEAM 2 | 0 |
| TEAM 3 | 0 |
| TEAM 4 | 0 |

FIG.21

MONTHLY AVERAGE INCOME STATEMENT

| DR1 | OFFICE | HOSPITAL | SNF | CPO | DRG | TOTAL |
|---|---|---|---|---|---|---|
| INCOME | 46226.4 | 1424.8 | 184.2 | 57.6 | 75.0 | 47968.0 |
| UTILIZED LABOR EXPENSE | 50738.8 | 1635.4 | 145.7 | 68.4 | 24.1 | 52612.4 |
| UNUTILIZED SUPPORT LABOR EXP. | 0.0 | 0.0 | 0.0 | 0.0 | 0.0 | 0.0 |
| UNUTILIZED DIRECT LABOR EXP. | 0.0 | 0.0 | 0.0 | 0.0 | 0.0 | 0.0 |
| OTHER INCOME | 150.0 | 0.0 | 0.0 | 0.0 | 0.0 | 150.0 |
| OTHER EXPENSE | 1162.0 | 93.1 | 281.3 | 4.6 | 179.4 | 1720.0 |
| NET INCOME | (5524.3) | (303.7) | (242.8) | (15.5) | (128.5) | (6214.7) |

FIG.22

METHOD OF DETERMINING TASK COSTS FOR ACTIVITY BASED COSTING MODELS

BACKGROUND OF THE INVENTION

The present invention relates to activity based costing of a business process.

Activity based costing (ABC) is a cost accounting methodology which seeks to distribute costs to individual business units (product, customer, service, business line, etc.) based on the activities needed to produce the service, product or desired output. ABC begins by identifying the activities that are required to produce products, services, and service customers. Costs are then determined for each activity. Total costs for a product, service, or customer are calculated by summing the costs of all activities necessary to produce that product or service, or to service the customer.

ABC is different from traditional cost accounting methods in three significant respects. Firstly, ABC focuses on providing costs for individual products, services or customers, where traditional cost accounting provides cost information about organizational business units such as divisions, plants or departments. Second, ABC allocates costs based on the work activities and resources consumed to produce products, services or to service customers. This is in contrast to cost accounting which allocates costs based on an arbitrary metric (an example would be allocating costs for four different business lines based on the percentage of revenue brought in by each business). Finally, ABC allows the measurement of the cost of not doing the work in such cases as machine downtime, waiting for required materials or tools, where traditional cost accounting only allows us to measure realized department or machine costs.

ABC information has both a strategic use and an operational use. At the strategic level, ABC information allows organizations to understand the true cost of producing products, services, and servicing customers. Knowing this allows organizations to shed products, services, and customers whose consumed resources are greater than the revenue they generate, or re-price these products, customers or services to generate a profit. An ABC system also allows businesses to determine the cost of "Not Doing" or hidden liability that stems from incomplete work. At the operational level, ABC information allows managers to focus in on processes and activities that consume large amounts of resources and re-engineer those processes to reduce costs and cycle time. Using ABC information, organizations can drastically change their cost structure to become more competitive.

Though ABC is widely used in manufacturing, it has been almost impossible to practice in service industries. Manufacturing accounting systems typically allow plant or division costs to be broken down to department costs, and then to machine costs, work group labor costs, machine materials cost, etc. Accountants can assign these small units of cost to specific activities, and then assign activities to products or customers. This process allow the creation of an ABC system. In service industries, accounting systems also track division or department costs. However, a large percentage of service business' department costs are labor costs. No system has been found for breaking down these costs and assigning them to activities in order to create an ABC model when workers switch between tasks and customers minute by minute. Typically service companies would use an arbitrary metric such as percentage of revenue to allocate costs, as discussed above. Another way would be to determine the amount of time out of total time spent on each business line or customer. There are two ways to accomplish this: asking an expert to render an opinion, and time sampling. Time sampling results are both inaccurate and un-duplicatable because time sampling is dependent on the process, skill of the operator, and the statistics of sampling. A time sampling subject also performs differently in a test environment than under normal conditions. An educated guess is less accurate because experts do not often recall accurately all of the activities or time required to perform a task. A solution to this problem has been required for many years. In Peter Drucker's article "The Information Executives Truly Need" (Harvard Business Review, January–February 1995, pages p. 54–62) it is stated on page 56 that "for most knowledge-based and service work, we should, within 10 to 15 years, have developed reliable tools to measure and manage costs and to relate those costs to results". It is accordingly clear that a solution to this problem has been required for some considerable time.

Several operator independent methods of task time measurement are presently in existence. An operator independent method of task time measurement is a method which analyzes any manual operation or method into the basic motions required to perform it, and assigns each motion a pre-determined time standard which is determined by the nature of the motion and the conditions under which it is made. These measurements are calculated in such a way that they are independent of any particular operator, and instead represent the time taken to carry out an activity or task as performed by a standardized person.

Predetermined-Motion Time Systems (PMTS) is such a methodology, and is based on the Methods Time Measurement (MTM) concept developed in 1948 by H. B. Maynard, G. J. Stegemerten and J. L. Schwab. MTM is defined as a "procedure which analyzes any manual operation or method into the basic motions required to perform it, and assigns to each motion a pre-determined time standard which is determined by the nature of the motion and the conditions under which it is made. The data is often the result of frame by frame analysis of motion-picture films involving diverse areas of work, as in the case of the MTM-1 methodology. MTM and PMTS are well known technologies available in the public domain. Details of the techniques used therein can be found in "R. M. Motion and Time Study: Design and Measurement of Work"; Barnes, 7th edition; 1980.

The data is generally used to establish fair labor standards by employers and unions, in terms of the number of times the motion can be reasonably expected to be achieved in a given unit of time, and also to measure productivity of employees. The information is also used to determine the number of production workers needed for a process, manufacturing production schedules and the amount and delivery times of materials.

A problem with both MTM and PMTS is that there are many body movement/distance combinations. For example, fundamental motions evaluated by PMTS systems include reaching, leg motions, moving, side stepping, turning, turning the body, applying pressure, bending, stooping or kneeling on one knee, grasping, kneeling on both knees, positioning, sitting, disengaging, standing from sitting, releasing, eye travel, walking, eye use, foot motions, and cranking. MTM and PMTS are accordingly unwieldy measurement systems.

PMTS was refined by K. B. Zandin and the H. B. Maynard and Company, Inc. in 1974 to produce a new proprietary product, the Maynard Operation Sequence Technique (MOST®). The development of MOST was the result of an extensive review of MTM data. The MOST system is based on the concept that work is the movement of objects, work being defined as force applied over distance. The human body moves in very specific patterns, each of which have an amount of work associated therewith. For example, the hands and fingers only work in certain ways, and the legs and arms only bend in certain ways. Through millions of lab observations, MOST has defined these patterns of human body movement as work is performed and assigned time values to each pattern and distance combination. MOST® has two unique characteristics which provide advantages over previous time management systems: 1) MOST is a scientific method that can be duplicated with an expectation that the generated time values will be the same for the same work process, as the results are independent of the operator. 2) The time values assigned to discrete tasks are accurate representations of the time in which it could be expected that the task be performed, within a 95% confidence that the value is within a 5% range either side of the "true" time required to perform a task at 100% effort and 100% skill and performing the task in the manner instructed. This is because the time generated is based on millions of lab observations. Clearly the time taken by an operator could be greater than this due to inefficiency in execution of the task or lower than this due to the operator not needing to perform certain parts of the tasks (particularly mental steps) or having particular dexterity due to years of practice. The measure does not try to establish a mean value, but essentially that of an ideal person performing the task exactly as instructed.

Details of the operation of the MOST technique can be found in Work Measurement, Kjell B. Zandin, 2nd edition 1993. There are two commonly used MOST methods as described in the above publication, referred to as basic MOST® and mini-MOST®. Mini-MOST is used for high frequency, low duration activities where accuracy is very important.

SUMMARY OF THE INVENTION

The invention provides a way of creating a costing model of a business that allows the underlying cost of carrying out a business process to be established, independently of the actual human operators involved in the operation of the process.

Removing factors dependant on the efficiency of the operators from the costs allows more accurate analysis to be achieved, as particularly skilled or unskilled operators working on a particular process could otherwise influence the perspective on the efficiency of an operation which could rapidly change along with a business's personnel.

The results of the process of the invention are used to establish financial profit, risk profile and quality of life in the business organization. The invention also allows businesses to measure the cost of "not doing" work in terms of hidden liabilities that exist when work is not completed. A financial model can be created which allows a service business to measure the utilization rate of resources, and by so doing allows the work tasks to be re-distributed to maximize the results or yield of every resource. Utilization ratios can be used to determine the quality of life of employees within a business. Risk profile of a business can be calculated by comparing the statutory or industry standards for a particular process with the measured business's process. The invention also allows businesses to conduct business scenario analyses, conduct calculations on return on investment (ROI), return on invested capital (ROIC) and internal rate of return (IRR). Furthermore, the invention allows the benefits of process improvements to be predicted and task time improvement requirements to be defined in order to meet specific goals.

The invention is particularly applicable to service industries. There are two types of benefits to creating an ABC model of a service business, strategic and operational. At the strategic level, if the revenue of different services or customers is known and the true costs of activities necessary to provide the service or service a customer are also known, then the true profitability of that service or customer can be ascertained. Service lines that are unprofitable can be terminated and customers who do not meet profitability goals can be re-priced or terminated. There are four additional strategic benefits that the invention provides.

Firstly, the invention allows the capacity of all resources to be compared with the sum of all activities using the resource. This allows the utilization ratio of the resource to be determined. The utilization ratio allows activities to be redirected to underutilized resources, and provides information regarding where additional capacity needs to be added to resources that are acting as bottlenecks to the flow of work through the process. By cross leveling capacity and adding resources, utilization ratios below 100% can be ensured. This improves quality of life and thereby reduces employee turnover. The risk associated with non-compliance with statutory or industry mandates is also reduced by ensuring the work processes and time meet specified requirements.

Secondly, the invention allows financial models to be created that predict the economic result of the addition of service lines, resources or process changes. This allows a service business to know in advance the economic result of business decisions.

Thirdly, the invention allows a service company to calculate the ROI, ROIC and IRR on any capital investment decision.

Finally, the invention allows service businesses to measure the unrealized cost of unperformed work which occurs when work is being performed in practice in less time than it theoretically should according to the model. For example, if a person sees a doctor and is given a plan of treatment, prescription and follow on appointment it might be thought that the service is complete. This is not the case. The physician must take several more actions before the service is complete. The doctor must identify the billing codes to be billed, dictate a note, transcribe a note, file the chart, bill a visit, etc. If any of these activities are not completed, the activity remains outstanding work that represents a hidden liability. In a service business, these liabilities can total millions of dollars. In a manufacturing industry, it is immediately evident that there is unperformed work, because the manufactured product will be incomplete.

At the operational level, the invention allows managers to determine which activities are consuming the most resources or time. With this knowledge, managers can implement re-engineering, Total Quality Management (TQM) or Statistical Process Control (SPC) processes to reduce costs and cycle time. The invention allows the operations manager to describe a new activity or technique and know the benefits immediately. Conversely, the invention can tell an operations manager how much of a resource or activity time must be reduced to meet a certain target benefit.

Furthermore, using this approach has the advantage of allowing operator performance to also be monitored relative to the non-operator dependant standards used, and allows the impact of an employee's efficiency on the profitability of the operation to be established, so that an employee can be appropriately compensated based on their performance.

The invention provides a method of performing costing of a work process including human activity and overhead costs. A list of tasks is established for said work process including tasks executed by a human operator. The expected duration of execution of the tasks is established using an operator independent method of task time measurement. A cost component of each task as a function of the expected time of execution of said task and the cost per unit time for said human operator is established along with a second cost component of each task dependent on overhead costs of the process. Portions of the overhead costs are apportioned to each task as a function of the time of execution of the task by the human operator, machine operating time or other relative consumption of resources. Finally, the cost components are summed for all the tasks to establish a process cost, and from the cost and revenue generated by the process, the profitability of the work process is determined, independently of the efficiency of the human operator.

In one embodiment of the invention, task times are developed using the MOST® system.

In a further aspect of the invention, activity based costing is performed to calculate costs of serving clients or customers in a service industry.

In a specific embodiment of the invention, activity based costing is performed to calculate costs of serving patients in a healthcare practice.

The invention provides a system for calculating the discrete time and cost for each work activity within a work process. Individual activity costs are then used to create financial models. These financial models can be created for an overall business, business lines, operation staffs and support staffs. A library of activity costs can then be used in any business analysis or projection.

BRIEF DESCRIPTION OF THE DRAWINGS

A specific embodiment of the invention will hereinafter be described with reference to the drawings in which:

FIG. 5 shows examples of charges for particular activities performed by a medical practice in an example of the preferred embodiment of the invention.

FIGS. 6 and 7 respectively show the drivers in the example of the preferred embodiment and the income generated thereby.

FIG. 8 shows how the sessions can be apportioned to each business practice in the example of the preferred embodiment.

FIG. 9 shows the fixed costs apportioned to each practice unit as a percentage of the total fixed costs in the example of the preferred embodiment.

FIG. 10 shows the total fixed costs apportioned to each practice based on the values shown in FIG. 9.

FIG. 11 shows the frequencies of certain events in the example of the preferred embodiment of the invention.

FIG. 12 shows the salaries of practitioners in the example of the preferred embodiment.

FIG. 13 shows unused provider hours in the specific example of the preferred embodiment.

FIG. 14 shows the practitioner cost per minute of the practitioners in the specific example of the preferred embodiment.

FIG. 15 shows the salaries of the support staff and the cost per minute in the example of the preferred embodiment.

FIG. 16 shows examples of the activity based costing performed in the example of the preferred embodiment.

FIG. 17 is a table showing calculation of the time taken by a department or provider to process one occasion of service.

FIG. 18 is a table showing calculation of the number of patients which can be treated per hour in the different practice.

FIG. 19 is a table showing a way of calculating utilization ratios based on restrictive and non-restrictive time.

FIG. 20 shows the utilization ratios of the departments and practitioners in the example of the embodiment based on the activity based costing performed or based on the calculations of FIG. 19.

FIG. 21 shows risk profiles generated from the utilization ratios of FIG. 20.

FIG. 22 shows a financial analysis of the data obtained in the example of the preferred embodiment.

DETAILED DESCRIPTION OF THE INVENTION

Figure 1:
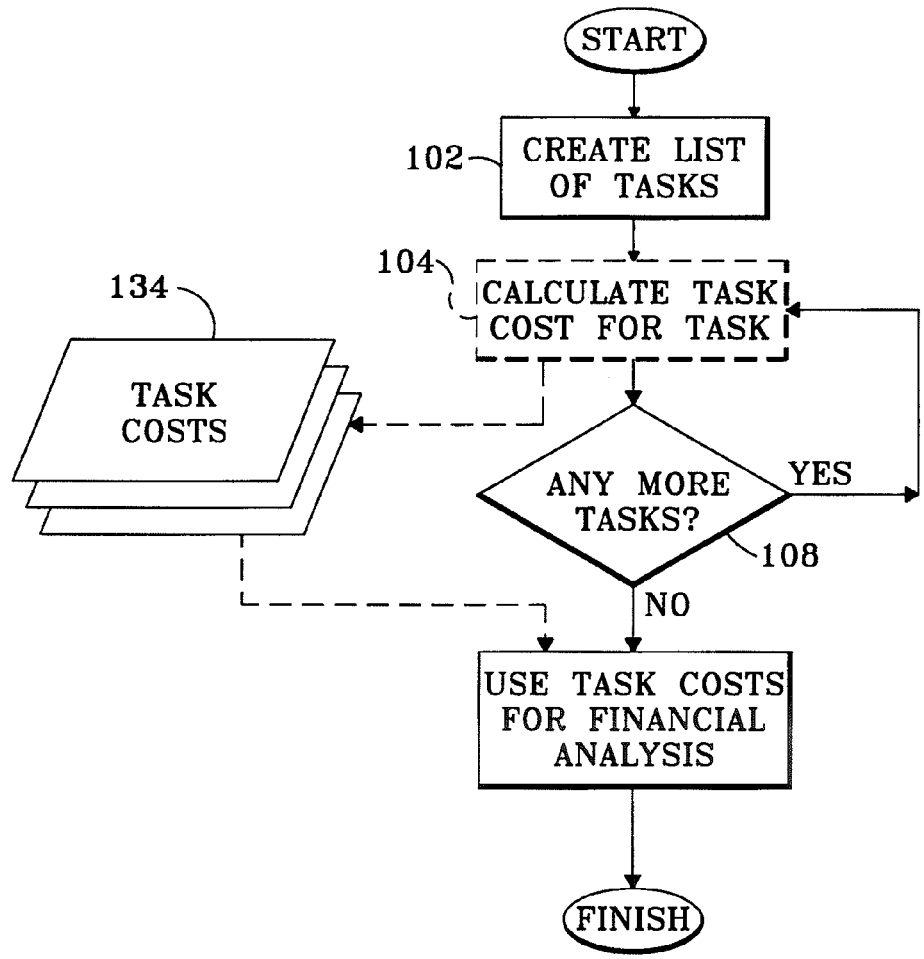
FIGS. 1 and 2 show an overview of the method employed according to the preferred embodiment of the invention.
Figure 2:
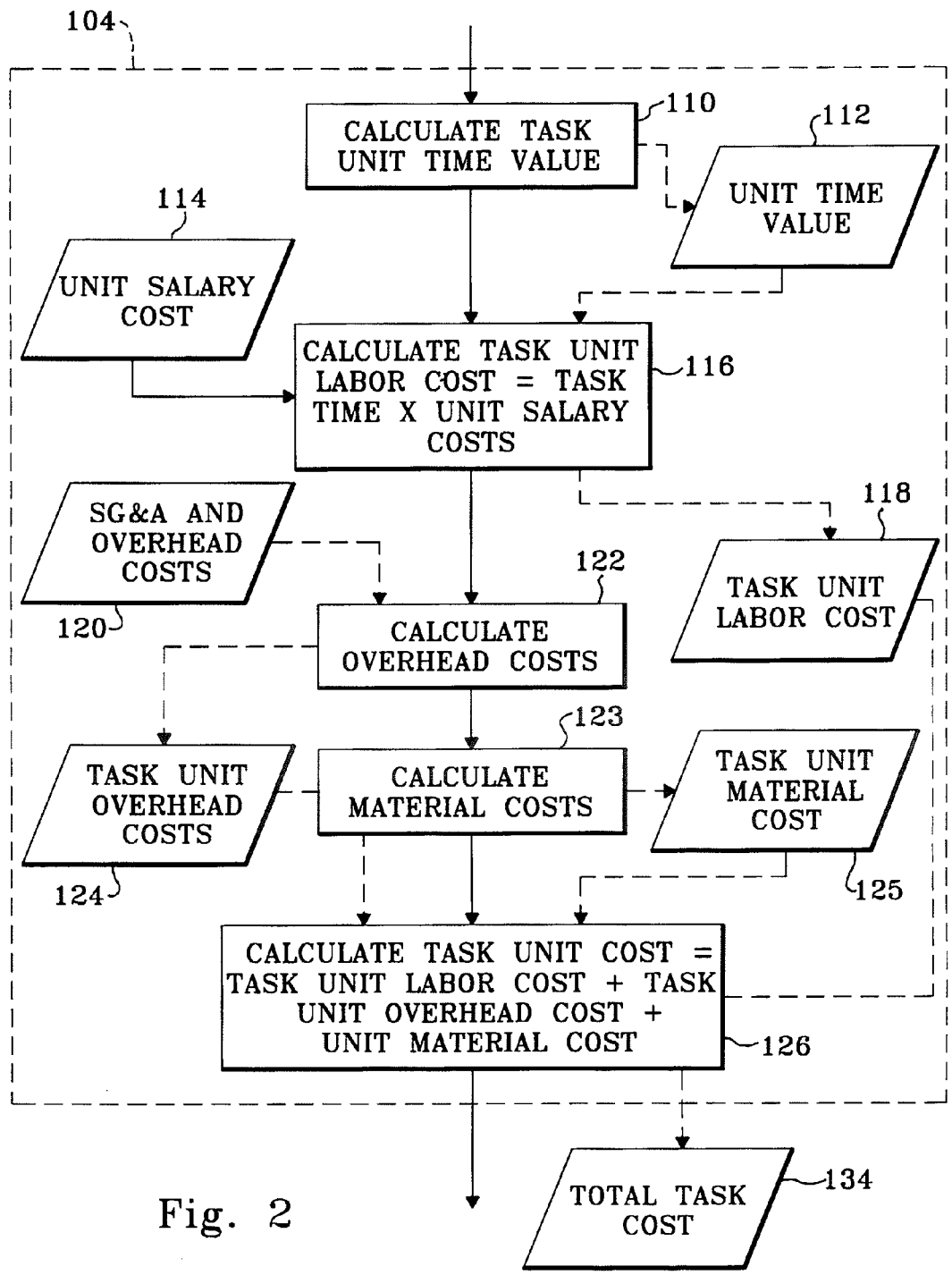
Figure 3:
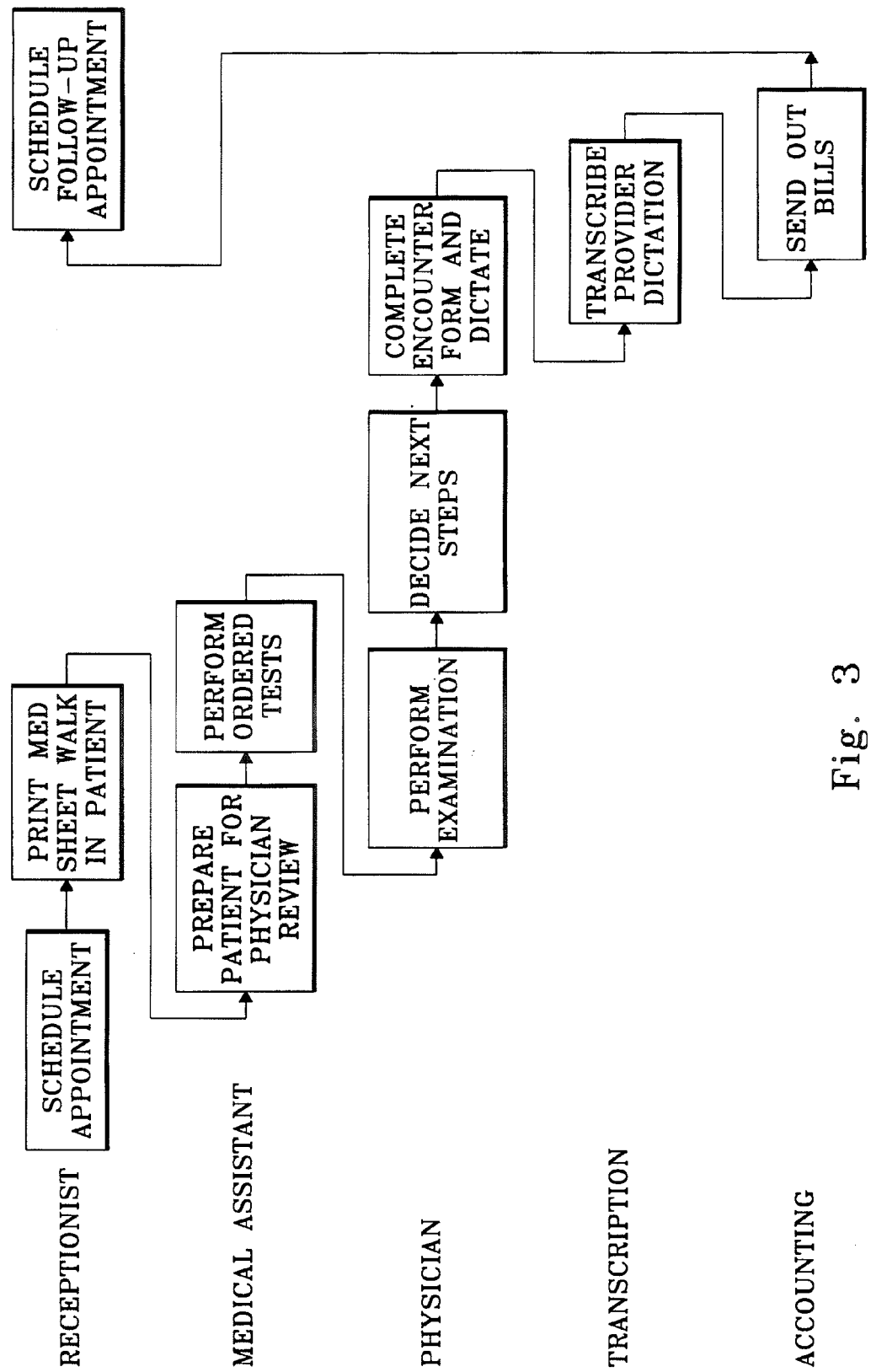
FIG. 3 shows a simplified example of flow-charted task activities performed by a medical practice in an example of the preferred embodiment of the invention.

An overview of the method of a specific embodiment of the invention is shown in FIGS. 1 and 2. An overview of the method is shown as two flowcharts, with solid lines showing the flow of operation, and dashed lines showing information being generated at each stage and used at further stages in the method. For clarity, FIG. 2 shows a series of steps represented by a single box 104 in FIG. 1. As shown in FIG. 1, firstly, a list of work activities or tasks is generated (step 102). Ideally, each department in a company is asked to create an exhaustive list of all work tasks performed. The task period cost 134 is calculated for the first task (step 104). Establishing the list of tasks will usually involve establishing different revenue generating work processes and breaking them down into tasks. These tasks can be flowcharted, and a simplified example of such a set of tasks is shown in FIG. 3 for an office visit in a medical practice. The tasks can be categorized by the operator performing the task, as in FIG. 3 to aid in costing, as will become clear. Some tasks might be common to more than one work process. This step is repeated for each task to obtain all the task costs for the process, as represented by looping decision box 108.

The steps required to calculate the task costs are shown in FIG. 2. It will be apparent that the steps shown in both FIGS. 1 and 2 could be performed in different orders to achieve the same end results, and that there are many equivalent combinations of calculations which could be performed based on the same values which would yield the same results. The sequence shown is in no way intended to be limiting, and other such sequences of calculations would be within the scope of the invention.

The first step (FIG. 2, 110) involves the calculation of task unit time values. Ideally a library of activity time costs is established in order to make this task simpler.

Each task is designated as a fixed or variable task. A fixed task is one whose time to complete has a low variance from a standard, doesn't occur very often and whose time to perform is easy to accurately measure. A variable task is a task not fitting these criteria. Each task is assigned a method of measurement. The methods of measurement will vary depending on the task's importance frequency and nature. The following four methods are utilized in this embodiment of the invention:
1) Expert Opinion is used when the task has no or few sub-components, is a task that requires analysis or thinking, is infrequent, not complex, and variation in performance of different operators is minimal.
2) Time study is often used when a task has multiple sub-components, has a low frequency and is not complex.
3) Industry Best Practice/Standards is often when a task is complex, has multiple sub-components, or the client dictates the value to be used. This would include government billing codes, such as Medicare codes presently used by the US government to standardize charges for performing certain activities in healthcare businesses.
4) A Pre-determined Motion Time System (PMTS) study using the Maynard Operation Sequence Technique (MOST®) is used when the task's sub-components can be identified, when the frequency of occurrence is high, and when the financial impact is high.

The decision regarding which method to use to a generate a task's time value is made on a task by task basis. The result of the implementation of these tools is a time value standard for every task.

In the next stage (FIG. 2, step 116), the Task Unit Labor Cost 118 is established by multiplying the task time 112 by the rate of pay 114 or Unit Salary Cost for each employee.

In the following stage (step 122), the Task Unit Overhead Cost 124 is calculated by allocating Sales General & Administration (SG&A) and overhead costs 120 to the task using the relative consumption of the resource. Such techniques establish what portion of the overhead and administrative costs are consumed by which activities and would normally include resource downtime in the costing.

Likewise, in step 123, the Task Materials Cost 125 is calculated by allocating the Materials Costs to the task using the relative consumption of the materials by the task.

Then, in step 126, the Task Unit labor Cost 118 and Task Overhead Cost 124 and Task Materials Cost 125 are summed to give the Task Unit Cost 128.

Figure 4:
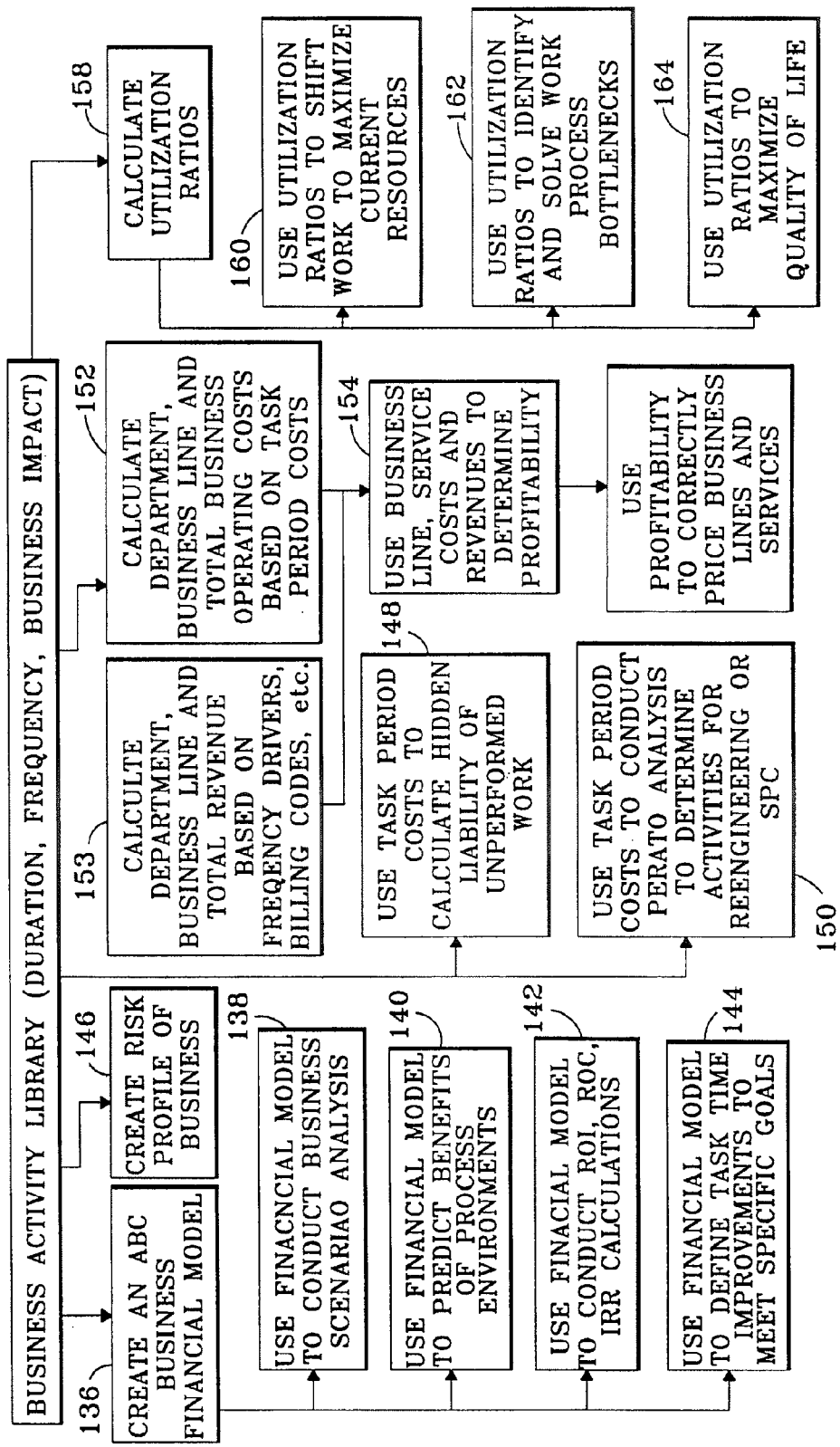
FIG. 4 shows analyses which can be performed using the data acquired by the process shown in FIGS. 1 and 2.

Once the steps 104 for each task have been performed for all the tasks, and a library of task costs has been developed, various different analyses can be performed on the data, as shown in FIG. 4.

For certain analyses, it is beneficial to multiply the task unit cost 128 by the period frequency of the task, which is generally established by interviewing or studying the operation of the task operator while working. This gives the Total Task Period Cost 134, which is the total cost of performing a task over a given period.

The task period costs 134 for a department can be summed, as shown in step 152 in FIG. 4 to give the department's total cost. These can in turn be summed to give business line and then total business operating costs. Task period costs can also be summed to determine the cost of providing a particular service.

As shown in step 158, the utilization ratio for different employees can be calculated for departments or staff and is defined as the time required to perform work divided by the time allocated for work at 100% skill and effort.

As shown in steps 160 and 162, utilization ratios can be used to conduct resource analysis which allows maximization of the yield of current resources and identify and solve work process bottlenecks.

Using utilization figures and staff constraints, a quality of life index for the business can be generated as shown in step 164. Performance rates can also be ascertained for the employees, based on the utilization ratio.

As shown in step 146, risk profile can be ascertained by dividing statutory or industry required hours to perform a given work load versus actual hours used for that work load. Excessively high ratios are an indicator of incomplete work or hurried activities and can be used to determine business liability and risk profile. Such analysis is beyond the scope of this document.

Using service, business line and total operating costs from step 152, and the revenue from step 153, the profitability of a service or business line can be determined along with its correct price as shown in step 154.

Using total ask period costs, the hidden liability of unperformed work can be calculated by determining the difference between required and scheduled hours and multiplying the difference by the department pay rate per hour. This is shown in step 148.

Using total task period costs, the activity costs are viewed from highest to lowest to identify those activities that would yield the greatest benefit in a reengineering, TQM, or SPC program. This is shown in step 150.

As shown in step 136, an electronic spreadsheet financial model of the service business is created using task frequency drivers, billing codes, insurance reimbursement schedules, reimbursement rules, and total task period costs. The economic output of the business can then be computed using the formula Revenue-Costs=Profit.

Using the ABC financial model created in step 136 different resources and staff members can be changed to determine the economic impact of business decisions as shown in step 138. The financial model can further be used to predict benefits of process environments as shown in step 140.

Using the ABC financial model created in step 136, activity times can be substituted to determine the benefit of process improvements and the results used to conduct ROI, ROIC, and IRR calculations to determine the pay-back of capital investment decisions. This is shown at step 142. Conversely, the activity time improvements and capital investment necessary to produce specific financial goals can be calculated as shown in step 140.

A specific example of activity based costing in accordance with the invention will hereinafter be described with reference to FIGS. 5–18. These figures mostly show tables of data which must be gathered from operational databases, business records and activity sampling. The example relates to a medical business which is funded in its capacity as a healthcare office, hospital, skilled nursing facility (SNF), Care Plan Oversight (CPO) and Clinical Drug Studies (DRGs).

The data in this specific example of the invention is stored in a computer and calculations are performed to manipulate the data to create a service business activity based costing model. According to this embodiment, a spreadsheet program such as Microsoft Excel is used to perform this task.

The data and the calculations shown in these figures are selected by way of example from a complete simulated analysis of a healthcare business. Similar models for other businesses will have different parameters, but the underlying principles will be similar.

The income generated by different types of examination or other revenue generating sessions in the practice are stored in the spreadsheet. Examples of some of the types of sessions and the charges associated therewith are shown in FIG. 5. The charges shown are for healthcare office and hospital revenue generating sessions. The Medicare code is shown in the first column, a description of the session type in the second column, the number of appointment slots used up by the session is shown in the third column and the fee associated with each session is shown in the fourth column.

Figure 7D:
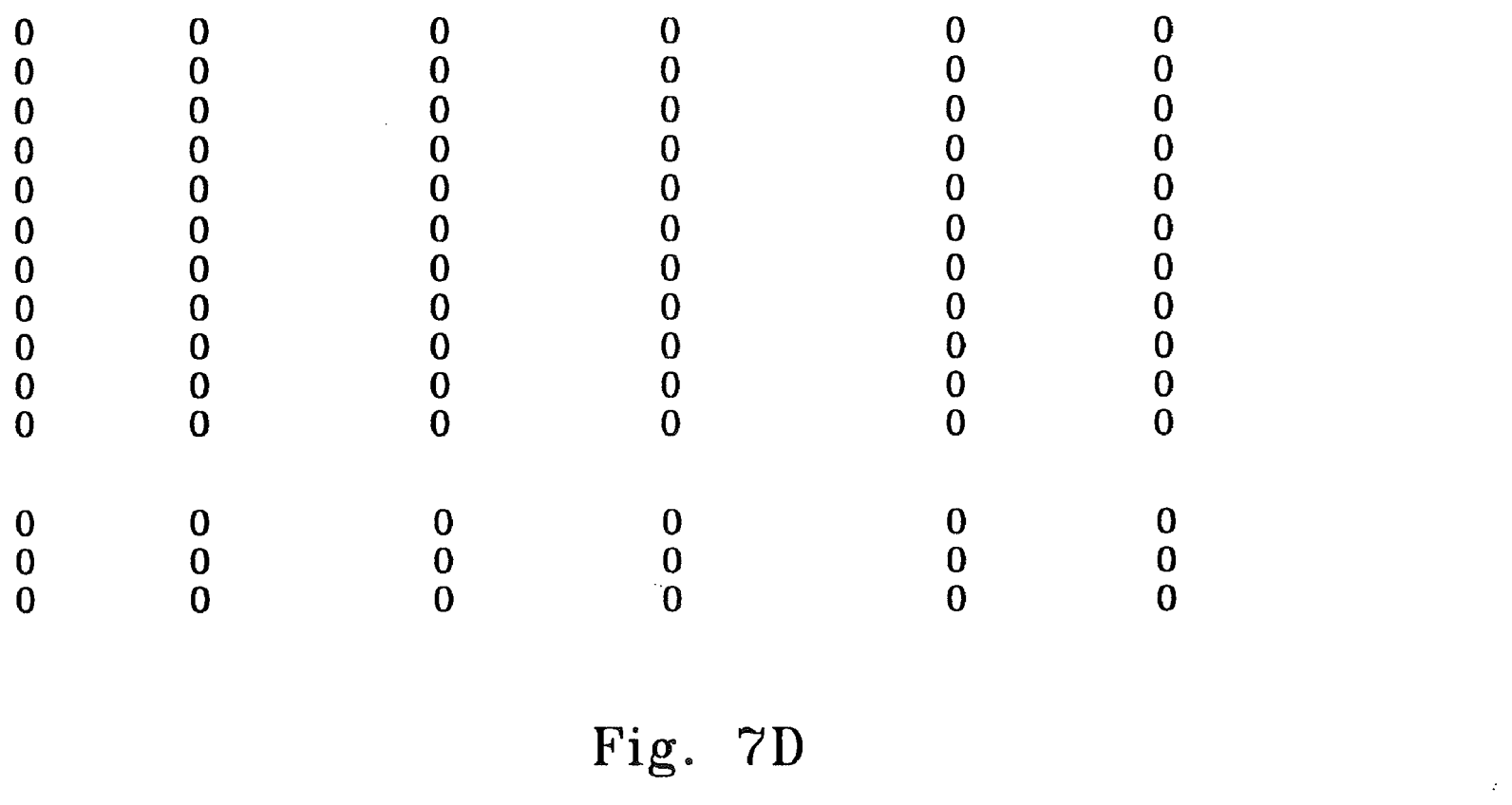

The number of actual sessions dealt with over a given period are also stored, as shown in FIGS. 6 and 7. These events are broken down by the practitioner or team of practitioners who deal with the sessions. For example, DR1 and DR2 represent the two physicians, and NP1 and NP2 represent the nurse practitioners. Different combinations of physician and practitioner both involved in a session make up the different teams. The sessions act as the drivers for the profitability of the practice. FIG. 6 shows the actual number of sessions in a month handled by the practitioners in the healthcare office. FIG. 7 shows the revenue generated by each session and the total revenue generated by each practitioner or team per month.

The session totals thus generated provide a straightforward way to apportion costs to the various types of practice in the business being analyzed. The totals generated are shown in the first table in FIG. 8. These values are shown as percentages of the total sessions for each type of practice in the second table. The third table simply shows the breakdown of sessions by practice type, and is based on the right-hand column of the first table.

The fixed costs of the operation are stored as shown in FIGS. 9 And 10. The actual costs per month are shown in the first column of FIG. 9, and the way the costs are apportioned to each of the practices is shown in the subsequent columns. Some of these are apportioned according to the number of sessions handled by the practices (eg. telephone, administrative salaries and computer expenses) using the data of the last table in FIG. 8, as they are more dependent on the actual number of cases handled by each practice. Others are broken down according to the physical size of the practice, such as rent, electricity and water. Others are broken down in other ways, such as office supplies which are broken down by the actual use of supplies by each department. This can also be monitored, or can be estimated statistically from studies of many practices. Once the fixed costs have been apportioned, the actual fixed costs for each practice can be calculated from the total fixed costs as shown in FIG. 10.

The support staff are required to track the number of times they perform certain operations over a certain period, and the results of this study are recorded in another table, shown in FIG. 11. A description of the event is shown in the first column. A numerical value of the frequency of the operation over the time period in question is shown in the third column and the unit of measure of the frequency is shown in the second column. The support department in question is shown in the fourth column.

The actual weekly hours are recorded, as shown in FIG. 12 along with the monthly salaries of the practitioners. Furthermore, the proportion of cases handled by the physician and the proportion handled by the nurse practitioner when they are acting as a team are stored for each different practice type. Finally, the available time of the practitioners is recorded as shown in FIG. 13, which can be used in conjunction with the actual hours worked to calculate the unused provider hours as also shown in FIG. 13.

With the information in FIG. 12, and knowing the number of work days per month, it is straightforward to calculate the cost per minute of the practitioners as shown in FIG. 14. The cost of teams is calculated by apportioning the cost per minute of the practitioners in the team according to the proportion of cases handled by each practitioner shown in 12.

The salaries and cost per minute of support staff is calculated in a similar manner, as shown in FIG. 15.

FIG. 16 shows a selected set of these activities performed by the receptionist department for an office visit, averaged for the practice and for a particular physician. Other activities involved in the visit by different departments, including costs of the practitioners are not shown, but will be included in the calculations. The second table in FIG. 16 is a set of calculations for a specific practitioner, in this case physician 1. Similar tables for all the other physicians are established, and all the values therein are averaged to give an equivalent table for the average cost of a visit in the practice as a whole. This table is the first table shown in FIG. 16.

The frequencies per month of the operations associated with Physician 1 are shown in the first row of the second table, and are generally ascertained from the drivers associated with that physician shown in FIG. 6, or from the frequencies of certain operations recorded by the support staff as shown in FIG. 11 multiplied by the percentage of sessions dealt with by each practitioner, ascertained from the data shown in FIG. 8.

The expected task time, in minutes, independent of the actual operator or support staff member, is established using the MOST® software. A library of such values would normally be created from which relevant activities are selected. The following row in the second table shows the percentage of visits in which the activity takes place, and the following rows show the time expended on the activity per visit. These columns are cumulative columns, summing across the row for each department and for the whole practice.

Finally, the monthly activity cost is calculated by multiplying the frequency of the activity, the task time and the cost per minute of the operator. These are cumulated over the department and the practice in the last two rows. Accordingly, average costs for a visit can be calculated when performed by each practitioner.

As mentioned above, all the values calculated for each practitioner in the second table in FIG. 16, and other equivalent tables for the other practitioners are then averaged over all the practitioners and teams to obtain the equivalent table for the whole practice, representing the average expected cost per visit at the practice.

The income generated by the process is essentially the amount paid for the service, in this case the cost of a visit to the practitioner. The profitability of a process, independent of the efficiency of the different human operators, can accordingly be calculated by subtracting the costs of the process from the revenue generated by the service. Using this information, decisions can be made regarding whether to continue providing certain services or products.

The table in FIG. 17 represents the time it takes one department or provider to process one occasion of service, including exceptions, in each of the business lines, in minutes. These values are lifted directly from the results of the calculations in FIG. 16. For example, it takes billing 15.17 minutes to process one hospital bill for an occasion of service. A doctor spends 23.52 minutes to see one patient in a nursing home visit. This chart is used to establish how long each type of service lasts and therefore costs.

FIG. 18 Shows the calculation of the actual and maximum patients per hour. First the average number of slots for an OOS for all types of patients, i.e. new patients, established patients and consulting patients is established by dividing the total number of slots used by the total number of OOS's, the data being obtained from FIG. 6.

From the schedule, the number of slots in the office are known, eg. 233 for the office per day. From the above calculation it is known that one patient OOS usually consumes 1.21 slots in the office. The number patient OOS's which can be provided per day or hour can therefore be calculated based on the number of slots per day or per hour. Enough time must be allocated for restrictive work activities to cover maximum patients per hour.

The final column is the number of patients actually being seen based on the schedule. The difference lies in patient cancellations or no shows.

A department's utilization ratio (time required to complete work/time allotted to accomplish work) can be calculated as shown in FIG. 19. The utilization ratio for a support department is not simply a straight calculation. It is known that some activities must occur when the patient is interacting with a support staff member. These tasks cannot be accomplished in the most efficient manner because they are dependent on the patient. These are referred to as restrictive activities. Other activities are independent of patients and can be accomplished in downtime. These activities are called non restrictive activities. Activities that are restrictive are established and the time calculated in FIG. 16 for each of the activities is summed (having been weighted by the proportion of OOS's for which the activity is required). This gives the average restrcitive time in minutes per OOS. Nonrestrictive time is calculated by summing the time spent by the department or practitioner in each practice (obtained from the table in FIG. 17) per OOS, weighted by the proportion of OOS's actually occur in each practice. The restrictive time per OOS is subtracted from this value to give the non restrictive time per OOS. The number of man hours required to cover restrictive activities by dividing the maximum patients that can be seen in one hour by the number of restrictive hours it takes to process these patients is then calculated. Based on the larger of the number of the actual or current patients per hour calculated in FIG. 18 and the restrictive time per OOS, the minium coverage in man hours per hour can be calculated. Depending on the number of man hours available (eg there are 8 provider man hours for any hour in the office practice), the unutilized portion can be calculated by subtracting the available time from the minimum coverage. The amount of time in one period that is not being consumed by restrictive activities is then calculated (Unutilized Portion Coverage). In the case of reception there is an Un-utilized portion of 80.77 hours available to accomplish non restrictive tasks (calculated from the number of hours per month available). Summing all non restrictive work for one period (by multiplying the number of OOS's by the non-restrictive time per OOS) gives the hours of non restrictive work that must be accomplished, in this case 490.6. The difference between the available un-utilized portion of monthly hours and the required time for non restrictive work gives us the amount of time per month (in this case 409.89 hours) that must be added to the restrictive period hours to give the total period hours that are required to accomplish restrictive and non restrictive tasks. Dividing the total available hours from the schedule by the total of restrictive and non restrictive hours yields an accurate utilization ratio.

FIG. 20 shows an alternative way of calculating of utilization ratios of the departments and practitioners based on the activity based costing performed. The first five columns of figures show the already calculated respective total hours which should have been required to carry out the activities by each department or practitioner in each practice using the PMTS technique used, and the totals across the whole business. The sixth column shows the actual hours worked, calculated from the values already recorded in FIGS. 14 And 15, and from these a utilization ratio can be established. A very high ratio implies that work is being hurried, or a backlog of follow-up work is building up, which could imply that standards are low leading to a high risk value as shown. The second ratio in this table is the ratio calculated using restrictive and non restrictive hours discussed above.

As these numbers demonstrate, when the support staff member is dependent on the patient or another input, tasks cannot be organized and accomplished in the most efficient way possible. Since the method described is attempting to get a true picture of the available capability of a department, this must be taken into account or the model will give misleading conclusions.

The risk profile follows the basic formula of number of hours worked/required time to service all the OOS's. This is relevant because by law, the doctor must spend a certain amount of time with the patient, which corresponds to the restrictive OOS time. Hence, the risk profile must be multiplied by an adjustment factor to eliminate the non restrictive time associated with an OOS. The adjustment factor simply eliminates non restrictive work from the calculation and is calculated from the ratio of non restrictive to restrictive hours.

Unutilized labor can be calculated where the utilization ratio is below 1 by multiplying a department or practitioner's salary per month by unutilized portion of the time (1-utilization ratio).

With this information, a financial analysis as shown in FIG. 22 can be made to calculate the theoretical costs for a work process attributable to each practitioner, team or the practice as a whole, for all its services, not taking into account the skill of the support staff. As the support staff could change dramatically over a very short period of time, it is advantageous not to take their skill into account when trying to establish the efficiency of the business and operating techniques used. FIG. 22 shows an analysis for one of the physicians, but it will be appreciated that the same can be done for the other practitioners and teams, and summed for each practice and the whole business. The income of the practices is ascertained by summing the data in FIG. 7 for each practice. The utilized labor expense is simply the result of the calculations shown in FIG. 16. Note that this labor expense isn't the actual labor expense (which is determined by the salaries of the staff) but is the theoretical labor expense independent of the actual skill of the support staff. The unutilized labor expenses are based on the values obtained form the analysis shown in FIG. 20. Any additional income over and above the income from examination sessions already taken into account is included at this stage, along with the fixed costs of the business, calculated in FIG. 10 which in this example are split evenly between the practitioners and teams.

This allows the overall theoretical profitability, independent of actual staff, to be calculated as shown.

To summarize, using Pre-determined Motion Time Studies, it has been shown that the capability is available to compute to + or −5%, with 95% confidence, the true time of completing a task. Armed with that information, the operator's pay rate can be used to compute the labor cost of a task, process, department, business line, product or service. Furthermore, a determination has also been made of the allocation of Sales and Group Administrative costs by applying those costs to the process tasks that consume them. In the process flow diagraming, the tasks have been identified which require materials and at what rate those materials are consumed. Summing the labor costs, S, G & A costs, and material costs allow us to determine the total costs of a task, process, department, business line, product or service.

It is known that businesses create value by producing a goods or service that a consumer requires at a price that the consumer is willing to pay. This process is called the value chain and represents a set of tasks that at their conclusion result in the exchange of the service or product for money. One of the first steps in the methodology is the identification of this value chain through process mapping. This activity is conducted in order to determine the costs of the value chain and also the revenue streams of products ad services generated by the value chain. Knowing revenue and costs allows us to implement the fundamental business formula: Revenue−Costs=Profit, to determine the true profit of a product, service, or business line. In the course of implementing the methodology, we have recorded the business' available resources, the value chain of activities required to produce a product or service, the consumption resources for each task or process and its associated costs, and the revenue of each product or service. Having completed all of the previous steps, we understand the relationships and timing of how inputted resources (labor, S, G & A, materials) become profit at the end of the value chain. These relationships are referred to as a financial model of the business. These relationships are stored as sequenced mathematical formulas. Because activity costs have been used to determine these relationships, the model is called an Activity Based Costing Financial Model. In this methodology, an ABC financial model is created for each product, service, business line, and for the total business. The ABC financial model is used to vary a business' resources (human labor, S, G & A expenses, and material consumed) and to be able to predict the economic result of these decisions. Though there are many applications of this information, 4 primary applications for this information are:

1. Reduced Risk—Business leaders can conduct "what if" scenarios to analyze the results of a change in resources. This allows a business leader to evaluate different courses of action to determine the best outcome. Having this information allows a business leader to reduce the risk of poor financial results, destruction of resources through overuse, or reduced regulatory compliance.
2. Financial Payback—From the above-mentioned use, the economic outcome of the application of resources can be determined. If the cost is known of the implementation of these resources and the interest rate, the return on investment (ROI) can be calculated. If the cost of borrowing money to the organization is known, the return on invested capital (ROIC) can be determined. The payback, or percentage return, of the business decision can also be established by calculating the internal rate of return (IRR).
3. Process Benefits—Using the ABC financial model, the current cost structure is known. If one or more processes is changed in the value chain, using the same methodology, the change in the cost structure of the product or service can be determined, and therefore the impact on profit, risk and quality of life. The old process can then be compared to the new process to determine the best method for accomplishing the necessary tasks in the value chain.
4. Quantification of Goals—Conversely, from the above use, an organization goal such as "reduce cost by 15%" or "improve net income by 5%," can be taken and the reduction of resources (labor, S, G & A, materials) necessary to achieve that goal can be determined.

Although the invention has been described by way of a preferred embodiment, other variations and modifications could be implemented and would still be within the scope of the invention.

The invention claimed is:

1. A method of performing costing of tasks including healthcare activities, said method comprising:
   a) establishing a list of healthcare tasks involved in a work process wherein said healthcare tasks involves execution by a human operator;
   b) for each task, determining:
      (1) how much the time to complete the task can vary from a standard with a single person and from person to person,
      (2) the frequency the task is performed,
      (3) how easy it is to measure the time to perform the task,
      (4) how many sub-components the task has,
      (5) whether the task requires analysis or thinking,
      (6) the complexity of the task,
      (7) if standard charges for the task by law exist, and
      (8) the financial impact of the task,
   c) for each task, deciding which one of four available methods of measurement should be used for calculating the duration of the task depending on the determining step, including:
      (1) expert opinions,
      (2) time studies,
      (3) industry standards, and
      (4) an operator independent method of task time measurement based on independently timing each motion in a procession of motions required to perform said healthcare task without timing from a beginning of said healthcare task to an end of said healthcare task a human performing said healthcare task;
   d) establishing a first cost component of each healthcare task as a function of the duration of said healthcare task and the cost per unit time for said human operator;
   e) establishing a second cost component of each healthcare task dependent on non-labor costs of the process, a portion of each non-labor cost being apportioned to said healthcare task as a function of the time of execution of said healthcare task by said human operator, machine operating time or other relative consumption of a resource;
   f) maintaining the expected time to complete said activities and the cost per unit time of said operator in a memory of a computer; and
   g) calculating a task cost using a processor of said computer including the step of summing the first and second components for the healthcare task to establish the cost of the healthcare task.

2. A method of performing costing of tasks including healthcare activities, said method comprising the steps of:
   a) establishing a list of healthcare tasks involved in a work process for a medical operating room or a medical examination room and including determining whether or not at least one of said healthcare tasks that involves execution by a human operator is a variable task determined to be a variable task by considering:
      (1) the variance of the time to complete the task determined to be a variable task relative to a standard,
      (2) how often the task determined to be a variable task occurs,
      (3) how difficult it is to measure accurately, (4) whether the task determined to be a variable task has identifiable sub-components, and (5) the financial impact to a healthcare business of which the healthcare activities are a part, b) calculating the duration of said at least one healthcare task determined to be a variable task by using an operator independent method of task determined to be a variable task time measurement based on independently timing each motion in a procession of motions required to perform said healthcare task determined to be a variable task without timing from a beginning of said healthcare task determined to be a variable task to an end of said healthcare task determined to be a variable task a human performing said healthcare task determined to be a variable task;

c) establishing a first cost component of each healthcare task determined to be a variable task as a function of the expected time of execution of said healthcare task determined to be a variable task and the cost per unit time for said human operator;

d) establishing a second cost component of each healthcare task determined to be a variable task dependent on non-labor costs of the process, a portion of each non-labor cost being apportioned to said healthcare task determined to be a variable task as a function of the time of execution of said healthcare task determined to be a variable task by said human operator, machine operating time or other relative consumption of a resource;

e) maintaining the expected time to complete said activities and the cost per unit time of said operator in a memory of a computer; and f) calculating a task cost independent of the efficiency of the human operator using a processor of said computer including the step of summing the first and second components for the healthcare task to establish the cost of the healthcare task.

3. A method according to claim 2 wherein the operator independent method of task time measurement is a predetermined motion time system.

4. A method according to claim 3 wherein the operator independent method of task time measurement is the Maynard Operation Sequence Technique.

5. A method in accordance with claim 2 wherein said healthcare tasks involved in said work process are executed by two or more different human operators.

6. A method in accordance with claim 2 wherein a utilization ratio of said operator is calculated based on the total task time calculated to be necessary to complete all tasks in all work processes executed by said operator and the total time worked by said operator.

7. A method according to claim 1 wherein a difference between the calculated time to complete a task independent of the operator and the actual time taken by the operator is used to establish a risk profile for the business, on the basis that a positive difference implies that work is not being carried out with the required care.

8. A method according to claim 2 wherein a difference between the calculated time to complete a task independent of the operator and the actual time taken by the operator is used to establish hidden liability of unperformed work, on the basis that a positive difference implies that tasks are being left incomplete.

9. A method in accordance with claim 2 wherein the healthcare tasks together form the work process, said method further comprising the step of:

f) summing the costs of the healthcare tasks in said process to give a process cost, and utilizing the process cost to determine the cost of the work process.

10. A method in accordance with claim 9 wherein the costs in the work process comprise the costs associated with a business unit.

11. A method in accordance with claim 9 wherein the costs in the work process comprise business line costs of a business line.

12. A method according to claim 11 wherein the business line costs and the revenue brought in by the business line are used to calculate the profitability of the business line, which is in turn used to correctly price the business line.

13. A method according to claim 9 wherein a financial model of revenue, costs and profit is created.

14. A method in accordance with claim 13 wherein at least one of ROI, ROC and IRR are determined for a capital investment.

15. A method in accordance with claim 9 wherein a business goal is set and changes in process cost and time are calculated.

16. A method in accordance with claim 9 wherein said method is further utilized to establish the cost of all work processes in said business.

17. A method in accordance with claim 9 wherein said operation costs comprise at least one of department costs and total business operating costs.

18. A method according to claim 9 wherein revenue generated by said process is calculated and profitability of said work process is calculated based on the difference between said cost of said process and said revenue.

* * * * *